(12) United States Patent
Moore et al.

(10) Patent No.: US 6,918,885 B2
(45) Date of Patent: Jul. 19, 2005

(54) VEST HAVING ARM SLING

(75) Inventors: Kenneth L. Moore, Osborn, MI (US); Shirley H. Moore, Osborn, MI (US)

(73) Assignees: Richard A. Young, Osceola, MO (US); Dorthy L. Young, Osceola, MO (US)

( * ) Notice: Subject to any disclaimer, the term of this patent is extended or adjusted under 35 U.S.C. 154(b) by 493 days.

(21) Appl. No.: 10/124,513

(22) Filed: Apr. 16, 2002

(65) Prior Publication Data

US 2002/0156406 A1 Oct. 24, 2002

Related U.S. Application Data

(63) Continuation-in-part of application No. 09/361,086, filed on Jul. 26, 1999, now Pat. No. 6,406,449.

(51) Int. Cl.⁷ .................................................. A61F 5/00
(52) U.S. Cl. ............................. 602/4; 602/20; 602/60; 128/878
(58) Field of Search ................. 602/4, 20, 21, 602/60, 61, 62; 128/846, 869, 873, 874, 878, 879, DIG. 19; 2/94, 102, 249, 250, 251, 252

(56) References Cited

U.S. PATENT DOCUMENTS

| | | | |
|---|---|---|---|
| 1,621,323 A | | 3/1927 | Horn |
| 2,344,844 A | | 3/1944 | Baldeschwieler |
| 2,512,474 A | | 6/1950 | Baldeschwieler |
| 2,549,703 A | | 4/1951 | New |
| 2,560,243 A | | 7/1951 | Peterson |
| 3,559,640 A | | 2/1971 | Beckett |
| 4,476,859 A | * | 10/1984 | Kloepfer et al. ............... 602/4 |
| 4,601,285 A | | 7/1986 | Whitchurch |
| 4,986,266 A | | 1/1991 | Lindemann |
| 5,072,456 A | | 12/1991 | Elin |
| 5,247,707 A | | 9/1993 | Parker et al. |
| 5,609,569 A | * | 3/1997 | Offenhartz .................... 602/61 |
| 5,628,725 A | * | 5/1997 | Ostergard ..................... 602/62 |
| D381,429 S | | 7/1997 | Millwood |
| 5,746,705 A | | 5/1998 | Sheppard |
| 5,772,617 A | | 6/1998 | Lay |
| 5,792,083 A | | 8/1998 | Joslin |
| 5,830,165 A | | 11/1998 | Rowe et al. |
| 6,110,133 A | * | 8/2000 | Ritts ............................ 602/4 |
| 6,453,904 B1 | * | 9/2002 | Wilson et al. ............... 128/874 |
| 6,485,445 B1 | * | 11/2002 | Hiltner ........................ 602/4 |
| 6,595,936 B1 | * | 7/2003 | Oladipo ....................... 602/4 |

OTHER PUBLICATIONS

North Coast Medical Catalog entitled "1999 ADL & Rehabilitation Catalog", pp. 10–11 (1998), depicting prior art sling designs.

* cited by examiner

Primary Examiner—Fadi H. Dahbour
(74) Attorney, Agent, or Firm—Hovey Williams LLP

(57) ABSTRACT

An arm sling assembly is disclosed for supporting at least one of the arms of a patient in an angled orientation against the torso. The assembly includes a sleeveless vest dimensioned to be worn on the torso of the patient. The vest is openable at the front to facilitate donning of the assembly. Moreover, attached to the one or both of the front portions of the vest is an arm support cuff. In particular, the support cuff is stitched to the front left or right portion of the vest along vertically spaced upper and lower attachment zones and is detached from the front portion between the zones so as to define an open-sided arm passageway in which the arm is inserted and supported. An alternative embodiment is also disclosed wherein the arm cuff is adjustably and removably attached to the vest at the upper attachment zone. This embodiment further includes a retaining strap that attaches to the back of the vest and encircles the supported arm(s), the arm support cuff(s), and a portion of the torso to securely retain the supported arm(s) against the torso of the patient.

19 Claims, 2 Drawing Sheets

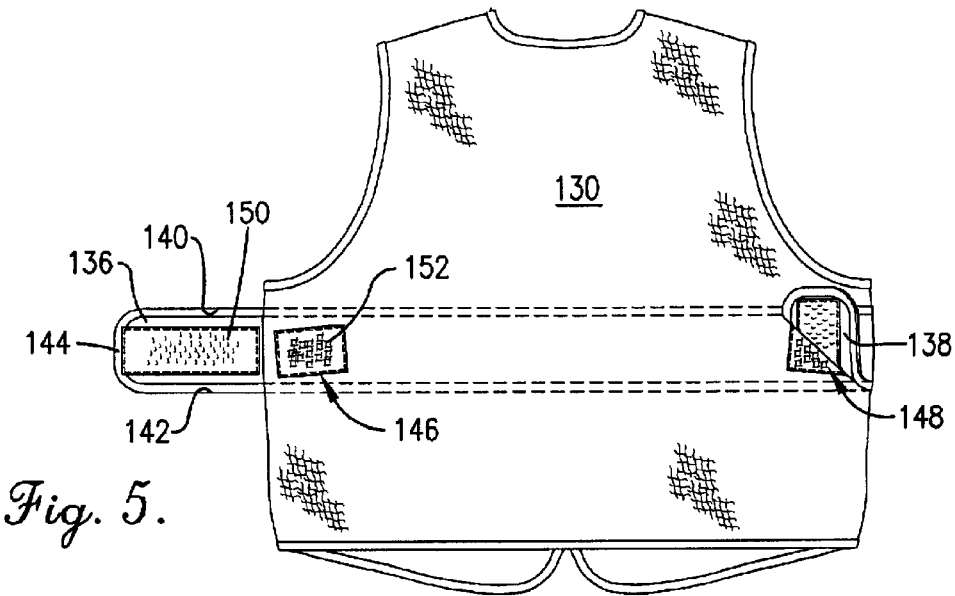
Fig. 5.
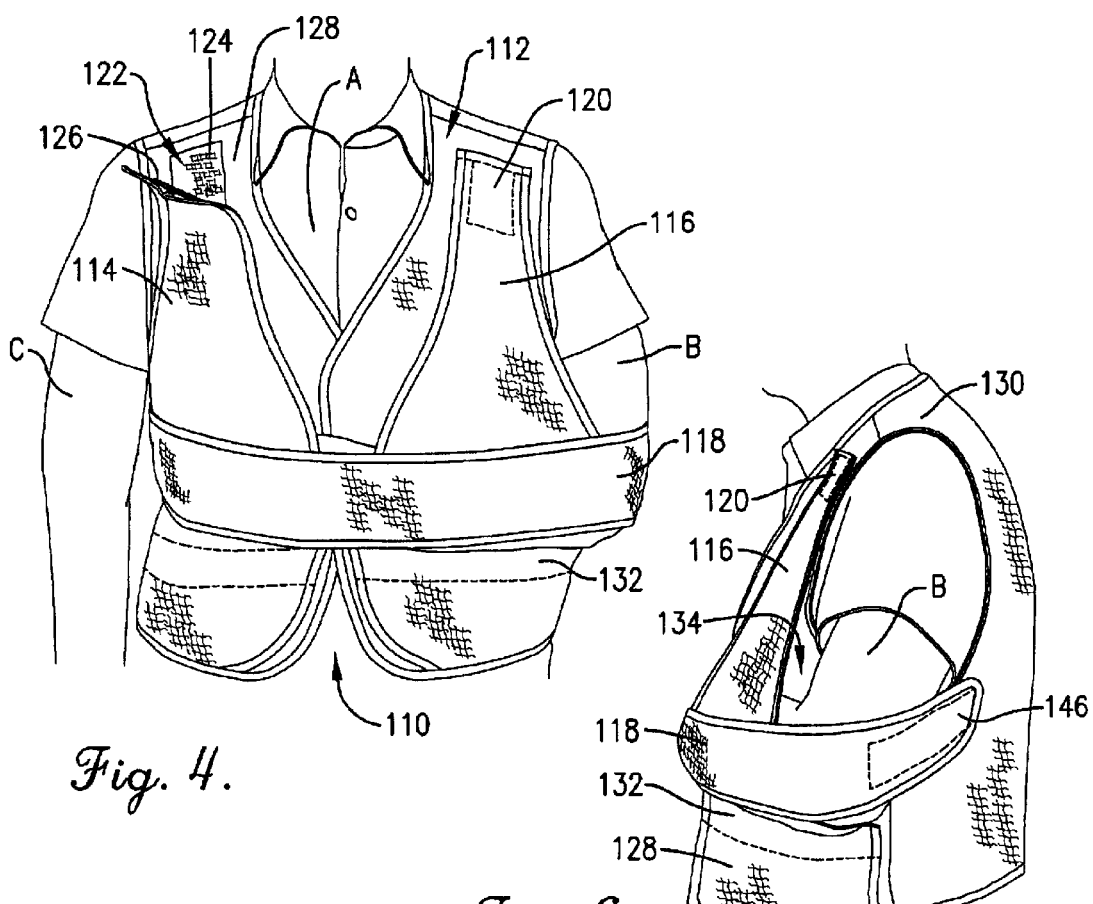
Fig. 4.
Fig. 6.

VEST HAVING ARM SLING

RELATED APPLICATIONS

This is a continuation-in-part of application Ser. No. 09/361,086 filed Jul. 26, 1999, now U.S. Pat. No. 6,406,449, which is hereby incorporated by reference herein.

BACKGROUND OF THE INVENTION

1. Field of the Invention

The present invention relates generally to medical products, such as arm slings. More particularly, the present invention concerns a generally sleeveless vest that is provided with an arm support cuff attached to the vest in a manner to present an adjustable open-sided arm passageway in which the arm is inserted and can be securely supported in an angled orientation against the torso of the body.

2. Discussion of Prior Art

It is common to support and/or immobilize the arm of a person in an angled orientation against the torso of the body as treatment for or a prophylaxis against injury to various parts of the arm or shoulder. For example, a fracture of the humerus will typically require the affected arm to be placed in a sling so that the arm is supported in an angled orientation against the torso.

However, there are numerous problems associated with conventional arm slings or supports. For example, traditional arm slings are often uncomfortable for the wearer and, in some extreme cases, may cause pressure ulcers. In particular, a traditional sling normally includes at least one strap that wraps around the neck or over the shoulder for supporting the arm cuff and thereby the arm in the desired orientation. The entire weight of the arm is consequently supported by the strap, and the strap concentrates this force on a very small area of the body. Additionally, traditional arm slings or supports are often difficult to don, particularly when the patient is attempting to put the device on without any assistance. The use of sling is also often perplexing, and this only adds to the difficulty in donning the device. Furthermore, conventional slings or arm supports are unsightly. Yet another problem with a number of traditional arm slings or supports is that they are not universal in the sense that they are designed for use with only the left or right arm but not both arms. Furthermore, traditional arm slings do not conveniently and securely support the arm against the torso so as to substantially limit shoulder movement.

SUMMARY OF THE INVENTION

The present invention provides an arm sling assembly that does not suffer from the problems and limitations of the traditional arm slings described above. The improved arm sling assembly of the present invention provides an adjustable arm passageway that allows variously sized patients to set the desired angled orientation of the affected arm relative to horizontal. Additionally, the improved arm sling assembly of the present invention provides a retaining strap for adjustably securing the arm and the arm cuff against the torso of the patient to substantially limit shoulder movement and prevent the arm from being inadvertently removed from the arm cuff.

A first aspect of the present invention concerns an arm sling assembly for supporting at least one of the arms of a patient against the torso. The arm sling assembly broadly includes a generally sleeveless vest dimensioned to be worn on the torso of the patient, and an arm support cuff attached to the vest. The vest includes a back portion, left and right front portions projecting from opposite sides of the back portions, and left and right arm receiving openings. The arm support cuff is attached to one of the front portions at vertically spaced upper and lower attachment zones and presents side margins which are detached from the one front portion between the attachment zones so as to define an open-sided arm passageway in which the corresponding arm may be inserted and supported. The arm cuff is fixedly and non-adjustably attached to the one front portion at the lower attachment zone. The arm cuff is adjustably and removably attached to the one front portion at the upper attachment zone so that the arm passageway is vertically adjustable relative to the one front portion.

A second aspect of the present invention concerns an arm sling assembly for supporting at least one of the arms of a patient against the torso. The arm sling assembly broadly includes a generally sleeveless vest dimensioned to be worn on the torso of a patient, an arm support cuff attached to the vest, and an elongated retaining strap operable to retain the arm cuff against the vest when the arm is supported in the arm cuff. The vest includes a back portion, left and right front portions projecting from opposite sides of the back portion, and left and right arm receiving openings. The arm support cuff is attached to one of the front portions at vertically spaced upper and lower attachment zones and presents side margins which are detached from the one front portion between the attachment zones so as to define an open-sided arm passageway in which the corresponding arm may be inserted and supported. The retaining strap presents opposite ends, each of which is attached to the back panel. The retaining strap is dimensioned and configured to at least partially encircle one of the arms and at least a portion of the torso of the patient when the assembly is donned.

A third aspect of the present invention concerns a method of supporting an arm of a patient in a flexed position against the torso. The method broadly includes the steps of inserting the arm into a sleeveless vest, supporting the arm in the flexed position on the vest with an arm cuff; wrapping a strap around the arm, the arm cuff, and a portion of the torso, and securing the strap to the vest to retain the arm and the arm cuff against the torso and to secure the arm in the arm cuff.

Other aspects and advantages of the present invention will be apparent from the following detailed description of the preferred embodiment and the accompanying drawing figures.

BRIEF DESCRIPTION OF THE DRAWING FIGURES

A preferred embodiment of the invention is described in detail below with reference to the attached drawing figures, wherein.

FIG. 4 is a front elevational view of an alternative embodiment of an arm sling assembly constructed in accordance with the principles of the present invention, illustrating the assembly being donned by a patient with the left arm being supported by the corresponding cuff and the left arm and corresponding cuff being securely retained against the torso by the retaining strap, and particularly illustrating the other cuff being folded back to reveal the complemental strips of hook and loop fastening material used to removably and adjustably attach the cuff to the respective front panel of the vest;

FIG. 5 is a rear elevational view of the arm sling assembly shown in FIG. 4, particularly illustrating the opposite ends of the retaining strap being folded back and/or detached to reveal the complemental strips of hook and loop fastening material used to removably and adjustably attach the opposite ends of the retaining strap to the back panel of the vest; and FIG. 6 is a left side elevational view of the arm sling assembly in use as shown in FIG. 4.

DETAILED DESCRIPTION OF THE PREFERRED EMBODIMENT

Figures 2, 3:
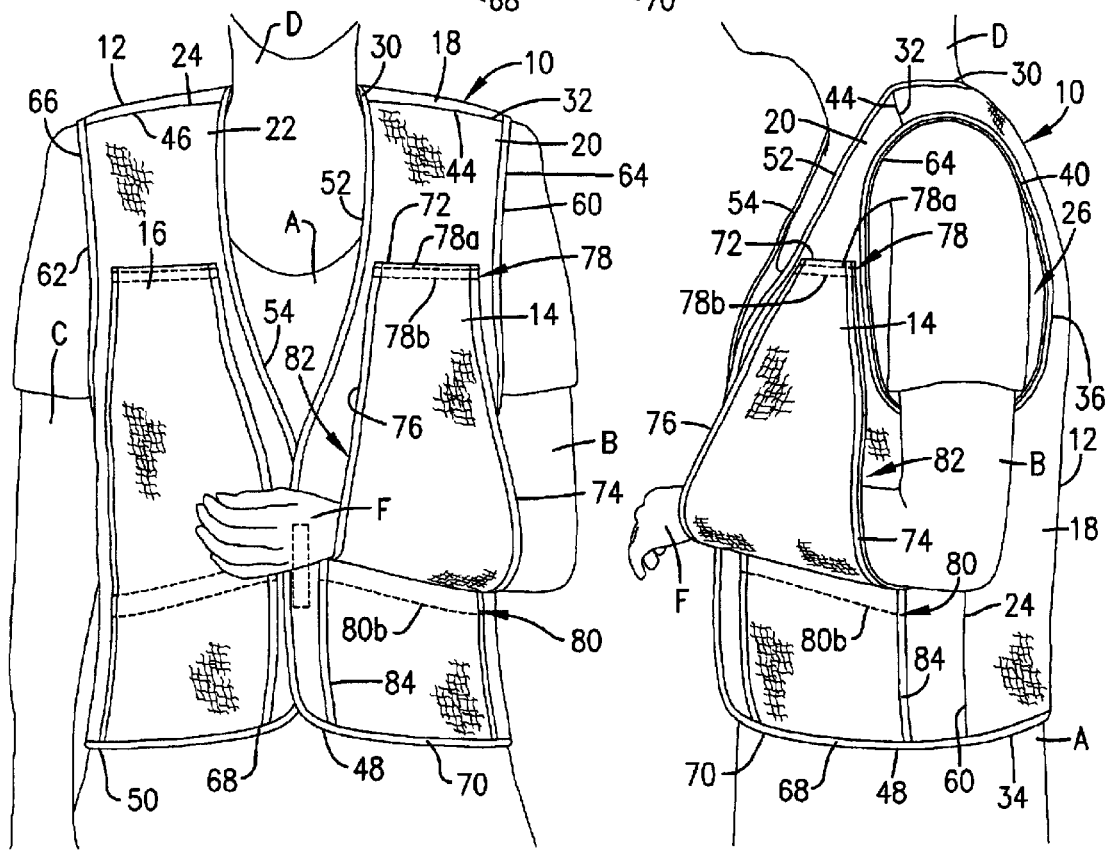
FIG. 2 is a front elevational view of the arm sling assembly similar to FIG. 1, but illustrating the assembly being donned by a patient with the left arm being supported by the corresponding cuff.
FIG. 3 is a left side elevational view of the arm sling assembly in use as shown in FIG. 2.

The arm sling assembly 10 selected for illustration generally includes a vest 12 and a pair of left and right arm support cuffs 14 and 16. As shown in FIGS. 2 and 3, the assembly 10 is dimensioned to be worn on the torso (A) of the patient and support either or both of the left and right arms (B) and (C) in an angled orientation against the torso (A). The assembly 10 will consequently be available in various dimensions to accommodate the various patient sizes. If desired, the assembly 10 may be custom fabricated for an individual's specific size.

The illustrated vest 12 is formed of a back cloth panel 18 and left and right front cloth panels 20 and 22 projecting from opposite sides of the back panel 18, although other suitable materials (e.g., a flexible plastic material)and configurations (e.g., a single, integral panel forming the front and back of the vest) may be used. The cloth panels are preferably interconnected by suitable means, such as the stitched seam 24. Left and right arm-receiving openings 26 and 28 are each cooperatively defined by the back panel 18 and the respective front panel 20 and 22. It should be apparent from the drawings that the openings 26 and 28 are oversized so that the arms (B) and (C) are easily and loosely received therein. In addition, the preferred arm-receiving openings 26 and 28 are formed in such a manner that the vest 12 presents no sleeves, which will further facilitate donning of the assembly 10. The illustrated vest 12 generally covers or overlies the thorax and abdomen of the patient; that is, the vest covers substantially all of the torso (A) above the waist. However, it will be appreciated that the principles of the present invention are equally applicable to various other vest configurations.

Figure 1:
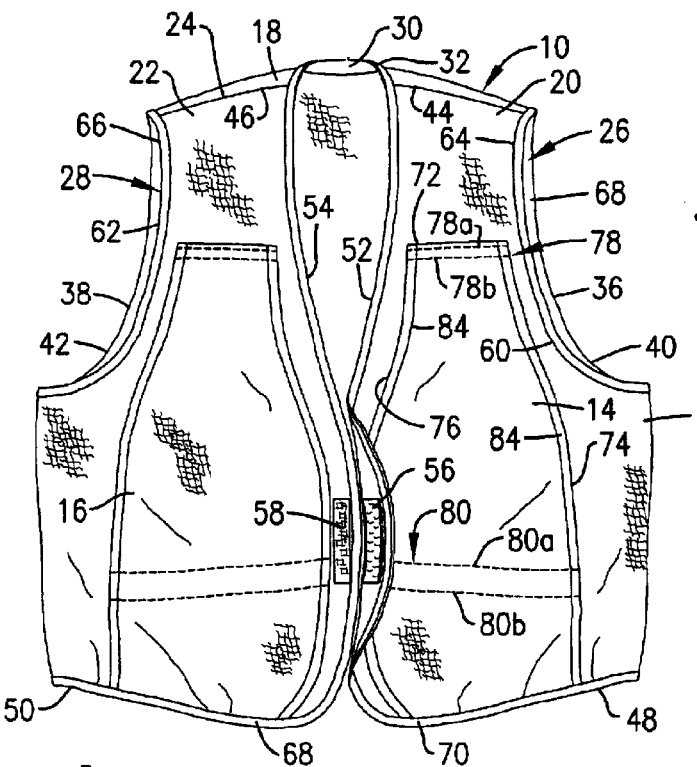
FIG. 1 is a front elevational view of an arm sling assembly constructed in accordance with the principles of the present invention, particularly illustrating the left front panel of the vest being folded over to reveal the complemental strips of hook and loop fastening material used to removably attach the overlapping sections of the front panels to one another.

As perhaps best shown in FIG. 3, the back panel 18 is dimensioned to overlie the back of the patient, extending generally from the buttocks to slightly over the top of the torso (A). A central, semicircular section 30 is defined in the top margin 32 of the back panel 18 so as to fit snugly around the posterior of the patient's neck (D), while the bottom margin 34 is generally straight and extends about the waist. The opposite left and right side margins 36 and 38 of the back panel include large, inwardly extending arcuate sections 40 and 42 (see FIG. 1) that define in part the respective arm-receiving opens 26 and 28, while the remaining sections of the side margins 36 and 38 are stitched to the respective panels 20 and 22 as noted.

Generally speaking, the front panels 20 and 22 are dimensioned to extend from the waist upwardly to the top of the torso, such that the panels 20 and 22 cooperatively overlie the anterior of the thorax and abdomen. The panels 20 and 22 are virtually identical in construction but are simply reversed in orientation relative to one another. As previously indicated, the stitched seam 24 attaches the top margins 44 and 46 of the panels 20 and 22 to the top margin 32 of the back panel 18. Similar to the back panel 18, the front left and right panels 20 and 22 present respective, generally straight bottom margins 48 and 50 that cooperatively extend around the front of the waist. It is noted that the illustrated vest 12 is openable at the front so that the panels 20 and 22 present separable, adjacent margins 52 and 54. As perhaps best shown in FIG. 1, the adjacent margins 52 and 54 extend tangentially from the semicircular section 30 defined along the top margin 32 of the back panel 18. Further, each of the adjacent margins 52 or 54 curves toward the opposite panel 22 or 20 as the bottom margin 48 or 50 is approached, such that the front panels 20 and 22 present an upper V-shaped opening and lower overlapping sections generally at the center of the torso (A). The illustrated vest 12 is provided with fastening structure at the overlapping sections so that the front panels 20 and 22 maybe releasably attached to one another, and the fastening structure is preferably in the form of complemental hook and fastener material strips 56 and 58 attached to the inside of the left panel 20 and the outside of the right panel 22. However, it is entirely within the ambit of the present invention to utilize various alternative fastening structure (e.g., a zipper, buttons, snaps, etc.) or eliminate the overlapping sections of the front panels 20 and 22 altogether so that the panels are not attachable. The front panels 20 and 22 also each present a side margin 60 and 62 including a respective arcuate section 64 and 66 and being otherwise stitched to the respective side margin of the 36 and 38 of the back panel 18. The arcuate section 64 cooperates with the arcuate section 40 of the back panel to define the left arm-receiving opening 26, and the arcuate section 66 cooperates with the arcuate section 42 of the back panel 18 to define the right arm-receiving opening 28.

The exposed edges of the vest 12 (i.e., the arcuate sections 40, 42, 64, 66; the bottom margins 34, 48, 50; the adjacent margins 52, 54; and the semicircular section 30) are preferably provided with a protective border 68. It is should be apparent from the drawing figures that, where possible, the protective border 68 extends continuously along the exposed edges of the vest 12. For example, a continuous border 68 extends along the bottom margins 34, 48, 50, the adjacent margins 52, 54, and the semicircular section 30. Preferably, the border 68 is formed of a cloth material.

The arm support cuffs 14 and 16 are preferably each constructed of a cloth panel, although other suitable materials may be used. The support cuffs 14 and 16 are virtually identical, and it shall therefore be sufficient to detailedly describe the left support cuff 16 with the understanding that the right support cuff 18 is similarly constructed.

The support cuff 16 has a generally trapezoidal shape and presents a lower margin 70, a relatively shorter upper margin 72 and a pair of downwardly diverging side margins 74 and 76. The lower margin 70 is stitched to the bottom margin 50 of the left front panel 20 and is covered by the protective border 68. Moreover, the support cuff 16 is attached to the left front panel 20 at vertically spaced upper and lower attachment zones 78 and 80. The upper attachment zone 78 preferably comprises a pair of relatively close stitching lines 78a and 78b adjacent the top margin 72. As perhaps best shown in FIG. 2, the top margin and stitching lines 78a and 78b are disposed in a generally horizontal orientation when the assembly 10 is donned. On the other hand, the lower attachment zone 80 comprises a pair of relatively further spaced apart, substantially parallel stitching lines 80a and 80b which slope upwardly toward the center of the torso (A) during usage of the assembly (see FIG. 2). It should be noted that the principles of the present invention are equally applicable to various other attachment zone configurations. For example, one or both of the attachment zones 78 and 80 may alternatively be formed by adhesive between the support cuff 14 and the front panel 20 (or some other means for attaching the support cuff 14 to the front panel 20 may be used). In addition, if stitching is used, the stitching need not be arranged in straight lines, as illustrated, but rather wavy, zigzag or other types of stitching patterns may be used, as well as less or greater stitching lines. It is also within the ambit of the present invention to provide discrete attachment points rather than the illustrated lines of attachment 78a, 78b, 80a, 80b.

The side margins 74 and 76 are not attached to the left front panel 20 between the stitching lines 78b and 80a, and an open passageway 82 consequently extends between the side margins 74 and 76. In the illustrated embodiment, the side margins 74 and 76 are also detached from the front panel 20 between the stitching lines 80a and 80b and between the lower stitching line 80b and the border 68, although it is entirely within the ambit of the present invention to attach the support cuff 14 to the panel 20 at these locations. Similar to the vest 12, the side margins 74 and 76 are provided with a protective border 84.

Thus, the vest 12 and support cuff 14 cooperatively provide means for supporting the left arm (B) in an angled orientation against the torso (A). It is particularly noted that the illustrated assembly 10 supports the left arm (B) in a slightly acute angle, which is often desirable to facilitate blood flow to and from the hand (F). This is primarily attributable to the location and orientation of the lower attachment zone 80. The lower attachment zone 80 is positioned at or just below the rib cage (not shown) of the patient during usage of the assembly 10. In addition, the stitching lines 80a and 80b preferably slope upwardly toward the center of the torso (A) at an angle between approximately five (5) and twenty (20) degrees relative to horizontal, with the illustrated angle of inclination being about fifteen (15) degrees. At least the upper stitching line 80a is configured to be readily removable in the illustrated assembly 10. This permits the cuff 14 to be detached from the vest 12 along this line, while the lower stitching line 80b preferably remains in place to define the lower boundary of the arm passageway 82. Those ordinarily skilled in the art will appreciate that the removal of the upper stitching line 80a permits, among other things, the patient to vary the vertical dimension of the passageway 82, the assembly 10 to support both large and small arms (e.g., an arm in a splint or cast as opposed to a bare arm) in the desired orientation, etc. The preferred trapezoidal shape of the cuff 14 ensures that a sufficient portion of the left forearm is supported, while not constricting the preferred generally V-shaped neck opening of the vest 12. It is also noted that the arm passageway 82 is open-sided as a result of both side margins 74 and 76 being detached from the panel 20. It is believed that this arrangement provides numerous advantages, such as permitting the hand (F) to rest naturally outside the confines of the passageway 82. Furthermore, the upper attachment zone 78 is preferably located generally over the left breast just below the left shoulder, when the vest is donned. This ensures that sufficient space is provide above the lower attachment zone 80 to receive the arm (B), while properly transferring the support load to the vest 12. A sufficient amount of "excess" material is preferably provided between the attachment zones 78 and 80 so that the support cuff 14 may expand slightly away from the left front panel 20 when the arm (B) is received therebetween (see FIG. 3), while still maintaining the arm (B) generally against the torso (A).

The right arm support cuff 16 similarly cooperates with the vest 12 to define an open-sided arm passageway (not shown) in which the right arm (C) is supported in a slightly acute, angled orientation against the torso (A). In this respect, the assembly 10 is universal in the sense that it may be used to alternatively or simultaneously support the arms (B) and (C).

In use, the vest 12 is first placed on the patient. This is accomplished simply by inserting the arms (B) and (C) into the oversized arm-receiving openings 26 and 28. The overlapping sections of the front panels 20 and 22 are then preferably attached to one another by bringing the fastening strips 56 and 58 into complemental interengagement. One or both of the arms (B) and (C) may then be inserted into the respective arm passageway 82 and consequently be supported in the desired manner. The assembly 10 serves to distribute the weight of the supported arm evenly from the corresponding shoulder to the neck. Further, there are no unsightly straps with the assembly 10, but rather the assembly generally has the appearance of a standard vest. As those ordinarily skilled in the art will appreciate from the foregoing description, the assembly 10 is easily put on the patient yet securely supports the affected arm or arms in the desired orientation.

As previously indicated, the principles of the present invention are equally applicable to various other attachment zone configurations. One suitable alternative configuration is embodied in the arm sling assembly 110 as shown in FIGS. 4–6. The assembly 110 is similar in many respects to the assembly 10, previously described in detail, and therefore the similar components and features will not be described in detail. The assembly 110 includes a vest 112 and a pair of left and right arm support cuffs 114 and 116, however the assembly 110 further includes an elongated retaining strap 118. The vest 112 and arm cuffs 114 and 116 differ from the previously discussed vest 12 and arm cuffs 14 and 16 in the manner in which the cuffs 114 and 116 attach to the vest 112 at the corresponding upper attachment zones 120 and 122, respectively. The upper attachment zones 120 and 122 are virtually identical in configuration and therefore only the upper attachment zone 120 will be described in detail. In particular, the upper attachment zone 120 comprises complemental hook and loop fastener material strips 124 and 126 fixed to the vest 112 and the arm support cuff 114, respectively. The hook and loop fastener material strips 124 and 126 can be formed of any suitable hook and loop fastener such as the hook and loop fastener available under the designation VELCRO. The material strip 124 is fixed to the outside surface of a front panel 128 of the vest 112. The material strip 124 is positioned toward the top of the front panel 128 adjacent the interconnection between the front panel 128 and a back panel 130 of the vest 112 (see FIG. 4). The material strip 126 is fixed to the inside surface of the arm support cuff 114 and is positioned toward the top of the cuff 114. Accordingly, the arm support cuff 114 is adjustably and removably attached to the front panel 128 of the vest 112 at the upper attachment zone 120. The arm support cuff 114 is fixedly and non-adjustably attached to the front panel 128 of the vest 112 at a lower attachment zone 132 in any suitable manner (e.g., the manner previously described with respect to lower attachment zone 80 of arm sling assembly 10). In this manner, the arm support cuff 114 is adjustably attached to the front panel 128 of the vest 112 so that the arm passageway 134 defined thereby is vertically adjustable relative to the front panel 128.

The vertical adjustability of the arm passageway 134 provided by the upper attachment zone 120 provides the arm sling assembly 110 with substantial versatility to allow a particular patient to support the arm (e.g., left arm (B)) in a flexed position (i.e., bent at the elbow) and to adjust the arm angle of the arm supported in the arm sling assembly 110 to achieve the most desired angle for the particular use. Furthermore, the vertical adjustability of the arm passageway provides an arm sling assembly that has somewhat universal versatility. That is to say, the arm sling assembly need not be a custom ordered manufacture but rather standard sizing could be utilized wherein a variety of variously sized patients could utilize the same size arm sling assembly yet still obtain a particular desired arm angle of an arm supported therein.

The retaining strap 118 is configured to securely retain one or both of the arm support cuffs 114, 116 against the corresponding front panel of the vest 112 when one or both of the arms (B) and (C) are supported therein. In particular, the illustrated retaining strap 118 comprises a detachable elongated cloth strap presenting opposite spaced apart ends 136 and 138. The strap further presents upper and lower side margins 140 and 142 extending generally parallel to one another between the ends 136 and 138. The exposed edges of the retaining strap 118 (i.e., at the margins 140, 142 and the ends 136, 138) are preferably provided with a protective border 144. The ends 136, 138 of the retaining strap 118 are each removably and adjustably attached to the back panel of the vest 112 at left and right attachment zones 146 and 148, respectively. The attachment zones 146 and 148 are virtually identically configured and accordingly only the left attachment zone 146 will be described in detail with the understanding that the right attachment zone 148 is similarly constructed. The end 118 removably and adjustably attaches to the back panel 130 at the attachment zone 146 by complemental hook and loop fastener material strips 150 and 152 (see FIG. 5). The hook and loop fastener material strips 150 and 152 are similar to the previously described hook and loop fastener material strips 124 and 126 and can be formed of any suitable hook and loop fastener. The material strip 150 is fixed to the inside surface of the retaining strap 118 adjacent or at the end 136 thereof. The material strip 152 is fixed to the back panel 130 of the vest 112 adjacent the left margin thereof and just below the arcuate section that forms a portion of the arm-receiving opening in the vest 112 (see FIG. 5). The retaining strap 118 is dimensioned and configured to at least partially encircle one of the arms (B), (C), at least one of the arm support cuffs 114, 116, and at least a portion of the torso (A) of the patient when the arm sling assembly 110 is donned by the patient (see FIGS. 4 and 6).

In this manner, when one of the arms (B), (C) is supported in the corresponding arm support cuff 114, 116, the retaining strap 118 can be wrapped around the supported arm and the supporting arm cuff and adjustably attached to the vest 112 to securely retain the supported arm against the torso of the patient. Such a configuration is desirable to substantially limit the movement of the supported arm (B), (C) and thereby substantially limiting the movement of the shoulder of the patient. In addition, such a configuration prevents the supported arm (B), (C) from inadvertently falling out of the arm support cuff 114, 116. It is important that the retaining strap have some adjustability in order to achieve the desired secure retention of the supported arm against the torso. However, it is within the ambit of the present invention to utilize various alternative configurations for the retaining strap. For example, the retaining strap could be non-removably fixed to the vest at one or both ends of the retaining strap to allow an integral formation of the retaining strap and the vest. Although such a configuration is within the ambit of the present invention, it is believed that this configuration is less preferable because it may be more difficult for the patient to don the retaining strap and properly adjust it. The retaining strap is preferably formed of a flexible material but it need not necessarily be cloth (e.g., it could be a flexible plastic material, etc.), however, the material preferably is sufficiently rigid to provide the desired secure retention of the supported arm against the torso when the retaining strap is donned.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. An arm sling assembly for supporting at least one of the arms of a patient against the torso, said assembly comprising:

a generally sleeveless vest dimensioned to be worn on the torso of the patient, said vest including a back portion, left and right front portions projecting from opposite sides of the back portion, and left and right arm receiving openings; and an arm support cuff being attached to one of the front portions at vertically spaced upper and lower attachment zones and presenting side margins which are detached from the one front portion between the attachment zones so as to define an open-sided arm passageway in which the corresponding arm may be inserted and supported, said arm cuff being fixedly and non-adjustably attached to the one front portion at the lower attachment zone, said arm cuff being adjustably and removably attached to the one front portion at the upper attachment zone so that the arm passageway is vertically adjustable relative to the one front portion.

2. The arm sling assembly as claimed in claim 1, said lower attachment zone sloping upwardly toward the center of the torso when the vest is worn.

3. The arm sling assembly as claimed in claim 2, said lower attachment zone sloping upwardly toward the center of the torso at an angle between approximately 5 and 20 degrees relative to horizontal, when the vest is worn.

4. The arm sling assembly as claimed in claim 3, said angle being approximately 15 degrees.

5. The arm sling assembly as claimed in claim 1, said arm cuff being adjustably and removably attached to the one front portion by complemental strips of hook and loop material.

6. The arm sling assembly as claimed in claim 1,
said lower attachment zone being generally linear and extending across the one front portion.

7. The arm sling assembly as claimed in claim 6,
said arm support cuff comprising a cloth article,
said lower attachment zone comprising stitching that interconnects the cloth article and the one front portion.

8. The arm sling assembly as claimed in claim 1,
said side margins diverging downwardly relative to one another from the upper attachment zone to the lower attachment zone.

9. The arm sling assembly as claimed in claim 1,
said upper attachment zone being located generally over the breast just below the shoulder and said lower attachment zone being located over the abdomen at or just below the rib cage, when the vest is worn.

10. The arm sling assembly as claimed in claim 1,
said arm support cuff being attached to the left front portion of the vest; and
a second arm support cuff being attached to the right front portion of the vest second vertically spaced upper and lower attachment zones and presenting second side margins which are detached from the right front portion between the second attachment zones so as to define a second open-sided passageway in which the right arm may be inserted and supported.

11. An arm sling assembly for supporting at least one of the arms of a patient against the torso, said assembly comprising:
a generally sleeveless vest dimensioned to be worn on the torso of a patient,
said vest including a back portion, left and right front portions projecting from opposite sides of the back portion, and left and right arm receiving openings;
an arm support cuff being attached to one of the front portions at vertically spaced upper and lower attachment zones and presenting side margins which are detached from the one front portion between the attachment zones so as to define an open-sided arm passageway in which the corresponding arm may be inserted and supported; and
an elongated retaining strap operable to retain the arm cuff against the corresponding front panel when the arm is supported in the arm cuff,
said retaining strap presenting opposite ends,
each of said opposite ends of the strap being attached to the back panel when the assembly is donned,
said retaining strap being dimensioned and configured to at least partially encircle one of the arms and at least a portion of the torso of the patient when the assembly is donned.

12. The arm sling assembly as claimed in claim 11,
each of said ends of the retaining strap being adjustably attached to the back panel.

13. The arm sling assembly as claimed in claim 12,
each of said ends of the retaining strap being removably attached to the back panel.

14. The arm sling assembly as claimed in claim 13,
each of said ends of the retaining strap being adjustably and removably attached to the back panel by complemental strips of hook and loop material.

15. The arm sling assembly as claimed in claim 11,
said back panel interconnecting with the left and right front portions below the corresponding left and right arm receiving openings,
said ends of the retaining strap being attached to the back panel at left and right attachment zones,
said left and right attachment zones being spaced apart and located generally below the corresponding left and right arm receiving openings and adjacent the interconnection between the corresponding left and right front portions.

16. The arm sling assembly as claimed in claim 11,
said arm support cuff being attached to the left front portion of the vest; and
a second arm support cuff being attached to the right front portion of the vest second vertically spaced upper and lower attachment zones and presenting second side margins which are detached from the right front portion between the second attachment zones so as to define a second open-sided passageway in which the right arm may be inserted and supported,
said retaining strap engaging the first-mentioned and second arm support cuffs so as to retain each cuff against the corresponding left and right front portion.

17. The method of supporting an arm of a patient in a flexed position against the torso, said method comprising the steps of:
(a) inserting the arm into a sleeveless vest;
(b) supporting the arm in the flexed position on the vest with an arm cuff;
(c) wrapping a strap around the arm, the arm cuff, and a portion of the torso; and
(d) securing the strap to the back of the vest to retain the arm and the arm cuff against the torso and to secure the arm in the arm cuff,
step (c) including the steps of attaching one end of the strap to one side of the back of the vest and wrapping the opposite end of the strap around the arm, the arm cuff, and a portion of the torso,
step (d) including the step of adjustably securing the opposite end of the strap to the other side of the back of the vest at a position spaced from where the one end of the strap is attached,
step (d) being performed after step (c).

18. The method as claimed in claim 17,
step (d) including the step of removably securing the opposite end of the strap to the other side of the back of the vest.

19. The method as claimed in claim 17,
step (c) including the step of adjustably and removably attaching the one end of the strap to the one side of the back of the vest.

* * * * *